United States Patent [19]

West

[11] Patent Number: 4,963,018

[45] Date of Patent: * Oct. 16, 1990

[54] RANGING APPARATUS

[75] Inventor: Robert N. West, Chislehurst, England

[73] Assignee: Sira Limited, Kent, Great Britain

[*] Notice: The portion of the term of this patent subsequent to Aug. 29, 2006 has been disclaimed.

[21] Appl. No.: 341,595

[22] Filed: Apr. 21, 1989

Related U.S. Application Data

[63] Continuation of Ser. No. 116,314, Nov. 4, 1987, Pat. No. 4,861,984.

[30] Foreign Application Priority Data

Nov. 10, 1986 [GB] United Kingdom ............... 8626812

[51] Int. Cl.$^5$ ........................... G01C 3/00; G01C 5/00
[52] U.S. Cl. ..................................... 356/1; 356/241; 356/4; 250/236
[58] Field of Search .............. 356/1, 4, 241; 250/236

[56] References Cited

U.S. PATENT DOCUMENTS

| | | | |
|---|---|---|---|
| 3,744,906 | 7/1973 | Sato et al. | 356/4 |
| 3,781,111 | 12/1973 | Fletcher et al. | 356/5 |
| 3,817,631 | 6/1974 | Kawahara | 356/1 |
| 4,331,975 | 5/1982 | Krawza | 358/100 |
| 4,440,496 | 4/1984 | Milana | 356/241 |
| 4,557,598 | 12/1985 | Ono et al. | 356/241 |
| 4,642,700 | 2/1987 | Ohta et al. | 358/285 |
| 4,717,823 | 1/1988 | Steimel et al. | 250/236 |
| 4,781,454 | 11/1988 | Cazenave et al. | 356/1 |
| 4,806,017 | 2/1989 | Sebastian et al. | 356/376 |

Primary Examiner—Stephen C. Buczinski
Attorney, Agent, or Firm—Sughrue, Mion, Zinn, Macpeak & Seas

[57] ABSTRACT

Apparatus for measuring the distance from the apparatus to a surface comprising means for passing a beam of light to the surface at an angle other than normal, means for receiving light reflected from the area of the surface illuminated by the beam and means for measuring the movement of the received beam whereby to measure the position of the surface area, means being provided to scan the surface.

8 Claims, 5 Drawing Sheets

RANGING APPARATUS

This application is a continuation-in-part of Ser. No. 07/116,314, filed Nov. 4, 1987, and now U.S. Pat. No. 4,861,984.

The present invention relates to a ranging apparatus, that is, apparatus for measuring the distance from the apparatus to a remote point such as a surface.

One arrangement of apparatus according to the invention to be described includes ranging the surface of a bored cylinder, and another arrangement of apparatus of the invention to be described includes ranging flat surfaces.

The present invention provides apparatus for measuring the distance from the apparatus to a surface comprising first optical means for passing a beam of radiation to the surface at an angle other than normal, second optical means positioned to receive said beam of radiation after it has been specularly reflected from the surface means for measuring the movement of the specularly reflected beam with respect to the optical axis of the second optical means whereby to indicate the distance from the part of the surface struck by the beam to the apparatus and means for scanning said beam across the surface.

In a preferred arrangement, the cross sectional size of the beam at the surface is 5 micron.

In a preferred arrangement the optical axis of the second optical means is at right angles to the optical axis of the first optical means whereby, if the illuminated area is at the focus of the second optical means, movement of the illuminated area will be in the focal plane of the second optical means.

Through the specification we will refer to "optical" and like expressions. It should be understood that the invention is not restricted to apparatus using radiation of optical (visible) wavelengths but radiation of other wavelengths may be used including infra-red, ultra-violet, x-ray and electron beams where necessary.

Preferred embodiments of the invention will now be described by way of example only with reference to the accompanying drawings, in which.

We will firstly refer to the apparatus shown with respect to FIGS. 1-6. The apparatus of these FIGS. 1-6 IS specifically designed for ranging and also for inspecting the surface of the wall 12 of a cylinder bore 10 having an axis 15 which cylinder bore 10 may be the cylinder bore of an internal combustion engine. Such a cylinder bore 10 is conventionally provided in a cast engine block, and is bored by means of a rotary tool; after boring the bore is honed by a finishing tool. In honing, the surface is finished by means of a light abrasive honing tool which rotates and passes down and back up the cylinder bore 10. It leaves on the surface of the cylinder bore wall a series of fine helical scratches formed as the tool passes down and back up the cylinder bore.

Figure 1:
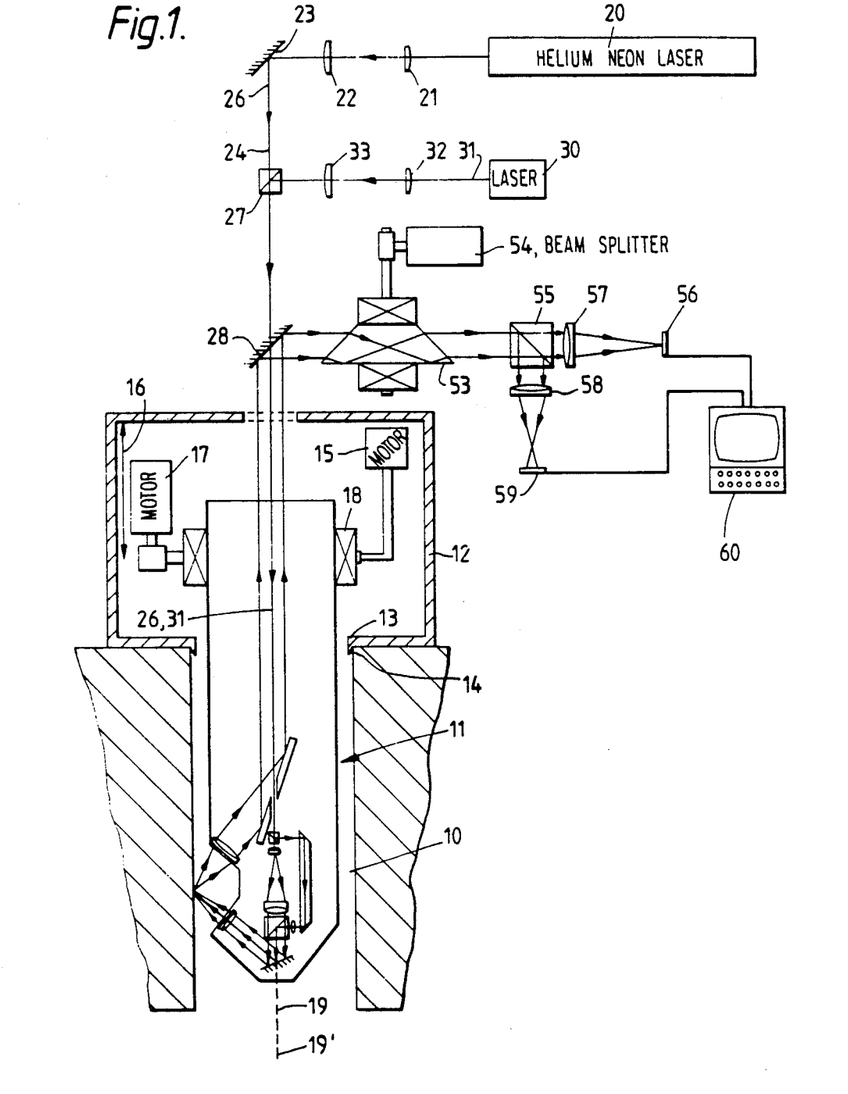
FIG. 1 is a diagramatic section of a first embodiment of the invention.

The apparatus for ranging and inspecting the surface of the cylinder bore 10 comprises a probe 11 mounted within the cylinder bore 10. The probe 11 is mounted within a housing 12, the housing 12 including an annular locating portion 13 which acurately locates with the top rim 14 of the cylinder bore 10.

The probe 11 is mounted within the housing 12 in such a manner as to be moveable up and down within the housing 12 by motor means 15 the movement being indicated by the arrow 16. The probe 11 is also mounted to rotate within the housing 12 by means of very accurate bearings indicated at 18 the bearings 18 being such that the lower end of the probe 11 rotates accurately about the axis 19 of the probe to an accuracy of greater than ± 0.25 minute of arc. The probe 11 may be rotated with respect to the housing 12 by means of a motor 17.

The optical components comprise a Helium Neon laser 20 providing a beam 26 of 633 nm wavelength; the beam 26 is shaped by means of collimating 18 lenses 21,22 and is reflected by means of plane mirror 23 onto the main optical axis 24 of the apparatus 24. The optical axis 24 corresponds with the axis 19 of the probe. The beam 26 passes through a beam combiner 27 through a central aperture in a plane mirror 28 and down through the probe 11.

A second laser 30 provides a beam 31 of 820 nm wavelength (infra red); the beam 31 is colimated by lenses 32,33 and is passed to the beam combiner 27 where it is combined with the beam 26 and passes down along the optical axis 24 to the probe 11.

Figure 2:
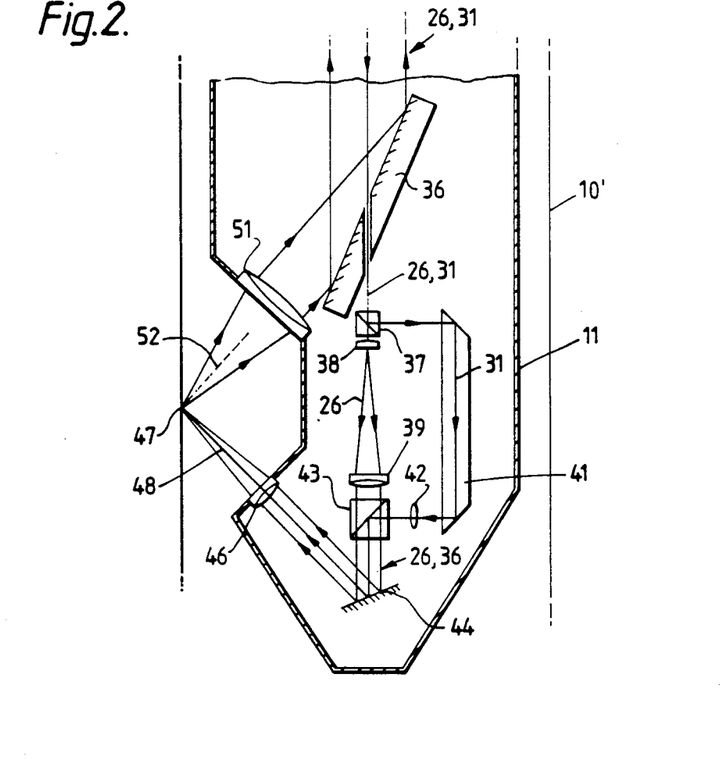
FIG. 2 is an enlargement of part of FIG. 1.

Details of the optical components at the lower end of the probe 11 are shown in enlarged size in FIG. 2. The combined beam 26,31 passes through a central aperture in a plane ,mirror 36 to a beam splitter 37.

The beam splitter 37 separates the two beam components 26,31, the infra red laser beam 31 being directed at right angles into an off-set path whilst the HeNe laser beam 26 passes on along the optical axis 24 to be expanded by two doublet lenses 38,39 acting as a telescope. The infra red beam 31 is directed around the telescope 38,39 by a prism 41.

After leaving the reflecting prism 41 the infra red beam 31 passes through a lens 42 and is then recombined with the beam 26 in a beam combiner 43. The combined beam 26,31 is then reflected by a plane mirror 44 towards a doublet lens 46 which focuses the HeNe laser beam 26 down to micron sized, typically 5 micron diameter spot 47 on the wall 12 of the cylinder bore 10.

On the other hand, the infra red laser beam 31 is shaped by the doublet lens 46 and lens, 43 to be a colimated beam of approximately 1 mm diameter at the cylinder wall 12.

As will be clear from FIGS. 1 and 2 the optical axis 48 of the lens 46 and hence the path of the combined beams 26,31 strikes the wall 12 at 45°.

The specularly reflected combined beam 26,31 is collected by a doublet lens 51. By choosing the angle between the optical axis 48 and the wall 12 to be 45°, the reflected beam axis 52 and wall 12 are also at 45°. The effect of this is that the optical axis 48 is at right angles to the axis 52 of the lens 51.

The doublet lens 51 collimates the reflected combined beam 26,31 and this is reflected out of the probe 11 by the plane mirror 36.

At the plane mirror 28 most of the light will be directed towards a dove prism 53 mounted so as to be rotatable about its axis by a motor 54. After passing through the dove prism 53 the combined beam 26,31 passes to a beam splitter 54 which separates the two beams, the HeNe laser beam 26 passing through the beam splitter 54 to be focused onto a position sensitive photo detector 56 such as a Sitech IL 2.5. The lens 51 and focusing lens 57 between the beam splitter 55 and photo detector 56 act to focus an image of the cylinder wall at 47 onto the photo detector 56 so that an image of the 5 micron diameter spot 47 is focused thereon.

Figure 3:
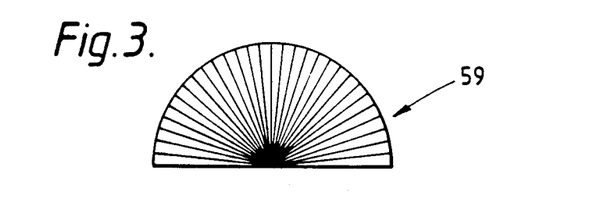
FIG. 3 is an enlarged alternative view of another part of the apparatus in FIG. 1.

The beam splitter 55 splits off the infra red beam at right angles through a lens 58 and passes the beam to a radial element detector array 59, a front view of which is shown in FIG. 3. The image on the array 59 is a far field image of the diffraction pattern of the beam at the wall 12.

It will be understood that in use as the probe 11 is rotated about its axis the image of the two beams on the detectors 56 and 59 would rotate in unison. This rotational movement is removed by rotation of the dove prism 53 at exactly half the angular speed of the probe (and in the same direction as the incident combined beam is rotating). Thus, the only motion of the images at the detectors 56 and 59 will be due to variations in the spot images at the cylinder wall 12.

Signals from the detectors 56,59 are passed to a suitable computer 60 where they are processed to produce the required measurements.

In use of the apparatus above described the housing 12 is firstly moved into engagement with the cylinder bore 10; in particular the annular locating portion 13 is accurately aligned with the rim 14. The probe 11 is then extended into the cylinder bore 10 and is rotated about its axis 19 which is coincident with the axis 15 of the cylinder bore 10.

The probe is rotated at whatever speed is desirable, which may be many thousands of revolutions per minute, typically 12000 revolutions per minute and the dove prism 53 is therefore rotated at half this speed 6000 rpm. It is intended to examine the complete wall surface of the cylinder bore 10 and so, because the spot size of the HeNe laser beam 26 on the surface is between 1 and 10 micron, typically about 5 micron in diameter, during each rotation of the probe 11, it should be translated upwardly (or downwardly depending on whether the probe is withdrawn or inserted during use) motor means 15 by a distance of approximately 5 micron to provide a continuous helix scan path. If however we are only interested in larger defects then we might for example withdraw the probe by 25 micron per rotation. Thus, although the speed of movement of the probe 11 will vary depending upon the minimum defect size that is to be detected, a typical rate of movement of the probe along this axis during operation might be 5 mm per second, so that a cylinder bore of 150 mm depth would be inspected in 30 seconds.

Consider firstly the HeNe laser beam 26. This is brought to a focus on the cylinder bore 10 wall and variations of the distance between the probe 11 and the cylinder wall will be recorded by the detector 56 as movements. This is because if the distance between the probe and cylinder wall increases then the apparent position of the spot to the lens 51 will move to one side of its optical axis, even though the spot remains in focus because the optical axis 48 along which the incident beam is passing is at right angles to the optical axis 52 and in fact lies in the focal plane of the lens 51. This relative movement of the spot is detected by the photo detector 56 and is sufficiently accurate that it may be used to provide output signals which may be processed by the computer 60 to measure the distance (ie range) from the probe 11 to the surface of the cylinder bore 10 and hence provide measurement of:

1. The diameter of the cylinder bore 10. (Measured by the absolute position of the image on the detector 56.)
2. The ovality of the cylinder bore 10. (Measured by variations of position of the image as the probe rotates.)
3. The straightness of the cylinder bore 10. (Measured by variations as the probe moves up or down the bore.)
4. The surface finish of the cylinder bore 10. (Measured by rapid random movement of the image.)
5. Surface defects which are effectively gross deviations of surface finish. (Measured similarly to 4.)

Under paragraphs 4 and 5 above surface defects such as scratches or pits will be recorded as changes in the distance between the probe and the cylinder wall and will be detected by movement of the focus spot on the photo sensitive detector 56.

It should be noted that the surface finish on the bore can be provided in CLA (Centre Line Average) terms.

In this way, the surface finish and the other features mentioned above can be detected.

The infra red laser beam 31 is intended to measure the honing angle, that is the angle between those fine scratches which are caused by the honing tool moving into the bore and out of the bore. The detection of this honing angle is based on the realisation that illumination of the surface of the cylinder wall by a relatively large spot will produce a reflected beam of star shaped cross-section, the arms of the star being caused by diffraction from the honing scratches and measuring the angle between the arms of the star allows one to measure the honing angle.

FIG. 3 shows a view of the radial element detector array 59. This radial detector array 59 comprises a series of detectors arranged radially and by measurement of the particular elements of the array which receive the most infra red radiation, that is those which detect the two arms of the star, one can provide a measurement of the honing angle.

The two separate functions of measuring the distance between the probe and cylinder wall and measuring the honing angle have been dealt with by two different lasers operating at different distinct frequencies which may be readily separated. In an alternative arrangement illustrated in FIG. 4 a single laser is used with a single beam and the two measurement functions are separated by using different polarisations of that single beam.

Figure 4:
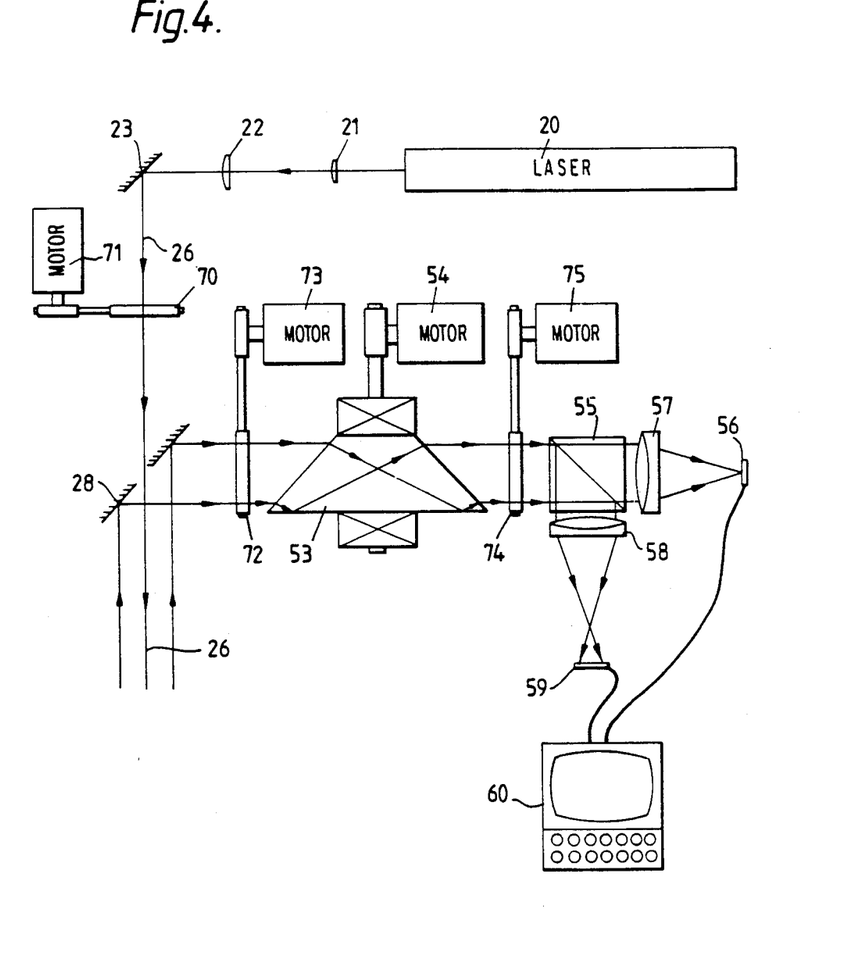
FIG. 4 shows an alternative arrangement of part of the apparatus of FIG. 1 providing a second embodiment of the invention.

Referring to FIG. 4 the laser 21 and optical components 21,22,23, and 28, 36 to 51 and 53 to 60 are retained but the laser 30 and optical components 32,33,27 are not present. Thus, there is provided a single beam 26.

Within the probe 11 the dichroic beam splitter 37 and beam combiner 43 are replaced by polarising devices. The plane mirror 28 is a dielectric mirror so as not to change the polarisation of the beam reflected therefrom.

Mounted in the beam path between the plane mirror 23 and mirror 28 is a halfwave plate 70 which is rotatable about the optical axis by means of a motor 71; between the mirror 28 and dove prism 53 there is provided a further halfwave plate 72 rotatable about the optical axis by a motor 73; and between the dove prism 53 and polarising beam splitter 55 there is provided a further halfwave plate 74 rotatable by a motor 75 about the optical axis. The motors 17,54,71,73,75 are arranged to rotate their various components as follows. If the angular velocity of rotation of the probe 11 is W, then motor 71 rotates halfwave plate 70 at W/2, motor 73 rotates halfwave plate 72 at 3W/4, motor 54 rotates dove prism 53 at W/2, and motor 75 rotates halfwave plate 74 at W/4. (All in the same direction.)

In use the laser 20 produces a plane polarised beam. The halfwave plate 70, by its rotation rotates the plane of polarisation of the beam so that it is rotating at the same speed as the speed of rotation of the probe 11. Thus, so far as the polarising beam splitter 37 is concerned, the plane of polarisation of the incoming beam remains constant even though the beam splitter 37 itself is rotating with the probe. The relevant phase between the rotation of the halfwave plate 70 and probe 11 is arranged so that the plane of polarisation of the incident beam on the beam splitter 37 will be such (ie 45°) that the beam splitter will equally divide the incoming beam between the straight through path through the lens 38,39 and the reflected diverted beam through the prism 41. (We can in some circumstances change the relative phase if for some purpose we require more light to pass in one direction from the beam splitter 37 than the other.)

Reflection of the beam from the wall 12 does not affect its polarisation. The optical components in the probe 11 provide at the surface of the wall 12 two portions of the beam, one producing a five micron diameter spot and the other producing a 1 mm diameter spot the two portions of the beam having polarisations at right angles to one another.

The beam returning to the mirror 28 is thus a combined beam of the two plane polarised beams (polarised at right angles), the planes of both of the combined beams rotating. In order to arrange for the two beams to be collected on the two detectors, the polarisation of each must be kept separate until the beams reach the final beam splitter 55. To maintain this condition the combined beam is passed through the halfwave plate 72 after reflection at the mirror 28. This halfwave plate maintains the relative phase of the two beams so that they can pass through the dove prism 53 unaffected.

Rotation of the plane of polarisation of the beam emerging from the dove prism 53 is removed by the rotation of the halfwave plate 73 so that the planes of polarisation of the combined beams when reaching the beam splitter 55 is stationary.

In this way the two beam components have been provided by differently polarised beams in place of the two beams of different wavelength. That is, the beam corresponding to the first beam 26 in FIG. 1 is provided having a first plane of polarisation by passing through the beam splitter 37, and a beam corresponding to the second beam 31 of FIG. 1 is provided by means of a beam passing through the prism 41 and having a plane of polarisation at right angles to that of the other beam component. In other respects the apparatus works as in FIG. 1, that is these two beams having been produced, although they are derived from the same beam, but are simply different polarisations, are then focused and treated in a different manner so as to be separable at the beam splitter 55 when the different effects can be registered by the detectors 56 or 59.

One of the difficulties of the arrangement so far described are that with respect to the beam spot of five micron in diameter, the depth of focus is very limited (typically 25 micron) and so, the 5 micron beam spot will only remain in focus over a very short distance. Although the position sensitive detector 56 can in principle measure the position of the "center of gravity" of the spot image thereon, it is unlikely that resolution of better than about 10% of the spot diameter could be achieved because of reflectivity changes of the surface (0.5 micron is the resolution need to measure the surface finish). Thus, extensive variations from cylindrical form can be difficult to measure and we must maintain the axis 19 of the of the probe and axis 15 of the cylinder coincident to less than 25 micron.

Figure 5:
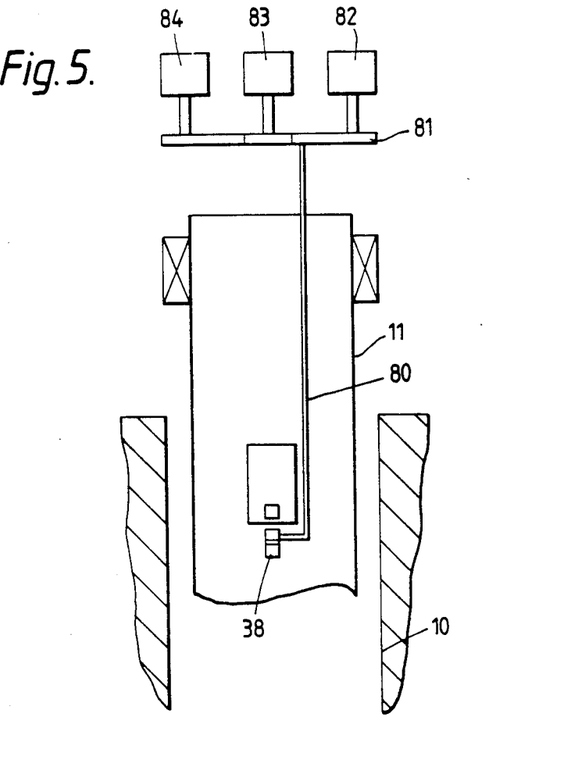
FIG. 5 shows an alternative arrangement of part of the apparatus of FIG. 1 or FIG. 4.
Figure 6:
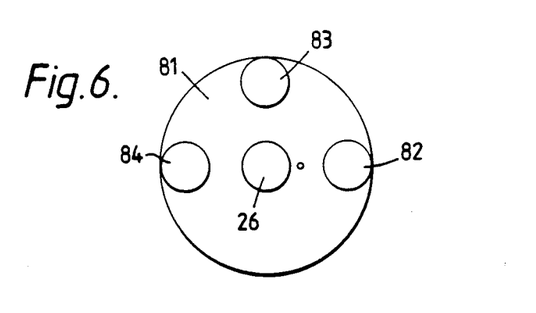
FIG. 6 is an end view of the apparatus of FIG. 5.

FIG. 5 shows an arrangement in which the 5 micron laser spot is provided by a variable focus means so that it is focused onto the cylinder wall so that greater variations of the cylinder wall from a perfect cylinder plus or minus 12 micron or greater disparity of the two axes 50 and 19 can be tolerated.

We provide a form of automatic focusing that responds relatively slowly during one revolution of the probe. In the arrangement shown in FIG. 5 the first doublet lens 38 is mounted so as to be moveable up and down with respect to the optical axis 24. The drawing is diagrammatic, but the lens 38 is mounted in a sliding bearing and is actually moved by means of a rod 80. The rod 80 passes up out through the top of the probe 11 and bears on the under surface of a non rotatable swash plate 81. The swash plate 81 is a flat plate which is normally arranged so as to be orthogonal to the optical axis 24, but which can be tilted from that orthogonal position by means of movement of actuators 82 to 84. If the swash plate is exactly orthogonal to the axis 24 then no longitudinal movement of the rod 80 takes place during rotation of the probe 11, but if the actuators 82 to 84 are actuated to tilt the swash plate out of the orthogonal position, then the rod will move up and down during each rotation of the probe to thereby move the lens 38. This changes the focal length of the telescope combination 38,39 and can be used to focus the five micron spot on the wall surface 12.

The servo signal to operate the swash plate actuators 82 to 84 is obtained from the position sensitive detector 56. In practice the actuators 82 to 84 only need to move relatively slowly and through very small distances because it is acceptable to take several rotations of the probe to get the swash plate into the right tilt situation. It can also be used to adjust the focus so as to be able to operate with different sizes of bore.

Another way of adjusting the focus is to move the lens 38 by means of a piezoelectric actuator which either acts directly on the lens 38 or else through a lever to increase the potential movement. The piezoelectric actuator can be fed with an electrical signal produced either through a mechanical arrangement or directly by means of signals from the position detector 56.

Whilst with the arrangement shown in FIGS. 1 to 6, ranging to the surface of the cylinder bore 12 is provided, because of the arrangement of the optical components within a probe 11 which rotates, it is clearly not suitable for ranging a flat surface.

Figure 7:
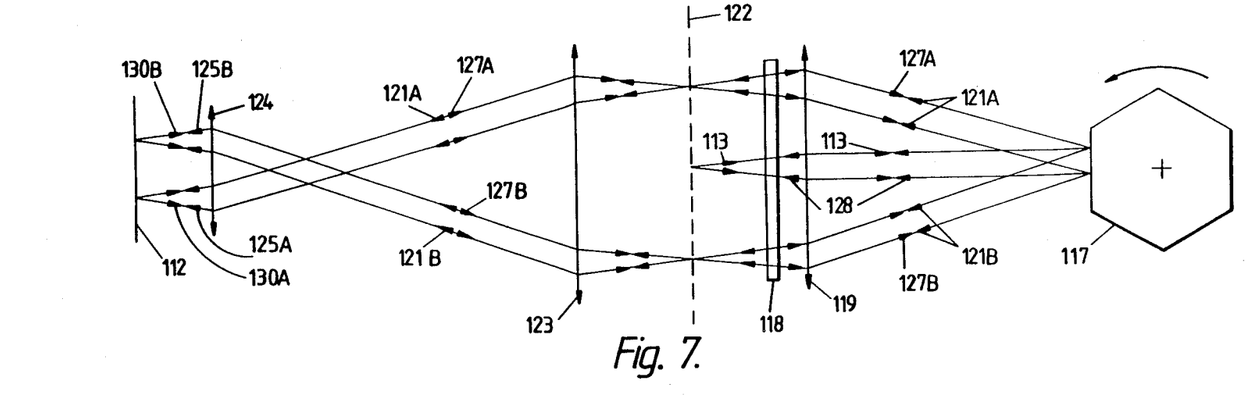
FIG. 7 is a diagrammatic plan view of the optical components of an apparatus providing a third embodiment of the invention, specifically adapted for ranging a flat or generally flat surface, and, FIG. 8 is a side view of the apparatus of FIG. 7.
Figure 8:
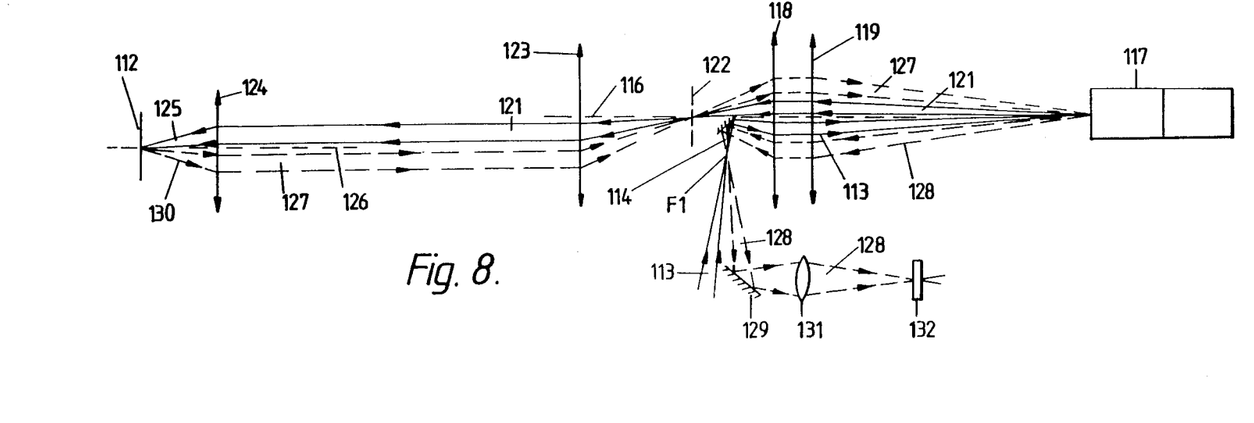

FIGS. 7 and 8 show an optical arrangement for ranging a flat surface 112.

It is necessary to provide an incoming and outgoing beam corresponding to beams 48,52 which are at the same angle to normal to the surface 112, and provide means for scanning across the flat surface 112.

Referring to FIGS. 7 and 8 there is provided a laser beam 113 which is focused to a first focal point F1, and thereafter passes to a small mirror 114. The small mirror 114 is in a position below (in FIG. 8) the optical axis 116 of the active optical components 118,119 to be described.

The beam 113 is reflected from the mirror 114 to a polygon mirror drum scanner 117 via a cylindrical lens 118 the axis of which is horizontal and a further lens 119. The outgoing beam (now numbered 121) reflected from the mirror drum scanner 117 is scanned between opposite limits (shown by beam 121A and 121B in FIG. 7) by the scanner 117. The beam 121 is brought to a focus along an intermediate scan line 122. The beam 121 then passes through a further lens 123 and lens 124, the lenses 123,124 providing an image of the intermediate scan line 122 on the flat surface 112, so that the beam is brought to a focus on the flat surface 112. The beam between lens 124 and the flat surface 112 is numbered 125.

The beam 125 is specularly reflected by the surface 112 and the return specularly reflected beam is indicated initiating as beam 130. The beam passes back through the lenses 124,123, (and is numbered 127 between lens 124 and mirror drum 117) is brought to a focus at the intermediate scan line 122, passes back through lenses 118,119 and is reflected by the same facet of the mirror drum scanner as the outgoing beam 121. The returning beam 127 is then reflected by the mirror drum scanner 117 back to the mirror 114 to a mirror 129, through a lens 131 and is focused by the lens 131 onto the front face of a position sensitive detector 132. The beam from scanner 117 to detector 132 is numbered 128.

It will be understood that the treatment of the beam (numbered at different parts of its path successively as 113,121,125,130,127,128) is different in the horizontal and vertical planes indicated by FIGS. 7 and 8.

Referring to FIG. 7, in this horizontal plane, the beam 113 from the mirror 114 is not affected by the cylindrical lens 118, but is only affected by the lens 119 and this is chosen so as to collimate the beam 121 in this plane as it passes from the lens 119 to the mirror drum scanner 117 and back to the lens 119. The lens 119 then focusing the collimated beam in this plane to a point on the intermediate scan line 122.

The lens 123 collimates the beam 121 in the horizontal plane of FIG. 7 and the lens 124 focuses this collimated beam onto the flat surface 112. In the horizontal plane of FIG. 7, the reflected beam 127 (the extremes of which, 127A and 127B are shown is treated by the various lenses and mirrors in the same way as the outgoing beam 12). Thus the beams 121 and, 127, overlap when viewed as shown in FIG. 7, arrows representing the particular beams 121,127 (or 121A, 121B, 127A, 127B)

The returning beam 127 is brought to a focus once again at point F1.

We now refer to the optical effect in the vertical plane, that is shown in FIG. 8.

Firstly it will be noted that the point F1 and the intermediate scan line 122 are confocal with respect to the lens system 118,119.

As has been noted before, the mirror 114 is below the optical axis 116 of the lenses 118,119 (strictly speaking of course lens 118 has an optical plane, rather than an optical axis, being a cylindrical mirror) and the disposition of the mirror 114 is such as to reflect the incoming beam 113 to a position where it passes through lens 118 below the optical axis 116. In this plane, the lenses 118 and 119 both act on the beam to bring it to a focus on the scanner 117 and the reflected beam 121 (which is now disposed on the opposite side of the optical axis 116 to the beam 113 is focused in this vertical plane by the lenses 118,119 onto the intermediate scan line 122. Because of the arrangement of the mirror 114 and its disposition below the optical axis 116 of the lenses 118,119, the beam 121 is also off axis, but above the axis 116 and then having passed through the intermediate scan line 1122 passes to lens 123. Lens 123 has an optical axis which is coincident with the optical axis 116. The lens 123 collimates the beam 121 in this vertical plane.

It will be noted that the lens 124, in this vertical plane, has an optical axis 126 below the optical axis 116 and, indeed, it is arranged so that the optical axis 126 is below the beam path 121 in this vertical plane. Thus, because the beam 121 strikes the lens 124 off axis, it is brought to a focus (as beams 125) on the surface 112 on axis, but from an off axis position and thus the incident beam 125 will approach the surface 112 from an angle other than normal. The reflected beam 130 will be reflected at an angle similar to the incident beam 125, but on the opposite side of the normal of the surface 112 (which is arranged to coincide with the optical axis 126, and then passes through the lens 124 off axis (in this case below the axis 126 in the view of FIG. 8), is focused by the lens 124 to form a collimated beam 127, is then focused by the lens 123 onto the intermediate scan line 122. Nevertheless, as is clear from FIG. 8, the beam 127 is further off axis than the beam 121 with respect to the lens 123 and so the returning beam 127 is further off axis with respect to the lenses 118,119.

The returning beam 130,127,128 is shown in dashed lines.

However, the lenses 118, 119 bring the returning beam 127 to focus as with the outgoing beam onto the scanner 117, the reflected beam 128 then passes through the lenses 119,118 onto the mirror 114. However, because the returning beam 127 is further off axis from the outgoing beam 121 it is the outgoing initial beam 113 so that the beams 113 and 128 are spatially separated, which means that the mirror 129 can be simply positioned to intercept the beam 128 alone.

It is, therefore, easy to separate the outgoing laser beam 113 and the returning beam 128, the returning beam 128 then passing to a mirror 129 through the lens 131 to the position detector 132. The position detector is similar to the detector 56 of the earlier embodiments (ie a Sitech IL 2.5) which can indicate the position of the incident beam.

It will be understood that different portions of the beam are numbered differently for ease of reference. Thus we have referred to the laser beam from the laser to the mirror 114 to the mirror drum scanner 117 by reference numeral 113, the outgoing beam reflected from the mirror drum scanner 117 via lenses 119,118,123,124 carries reference 121 or 121A or 121B, the beam from the lens 124 to the surface 112 carries reference 125,or 125A, or 125B the beam reflected from the surface 112 and passing to the lens 124 carries reference 130,130A,130B, the continuation of that reflected beam from lens 124 via lens 123, lens 118,119 to the surface of the mirror drum scanner 117 carries reference 127,127A,127B, and the returning beam reflected from the mirror drum scanner 117 carries reference 128.

It will be noted that the configuration of FIG. 8, so far as the beam 125, beam 130, and flat surface 112 are concerned is similar to the beams 48,52 and surface 12 of FIG. 2. Thus, the beam 125 passes to the flat surface 112 at an angle other than normal, is reflected from that surface as a reflected beam 130, the beam itself being focused Onto the flat surface 112.

However, in place of the separate lenses 46,51 in FIG. 2, a single lens 124 is provided. Because of this, the angle between beams 125,130 is usually less than the 90° of FIG. 2.

The point at which the beam 125 strikes the flat surface 112 is scanned back and forth (as shown in FIG. 7) by means of the scanner 117.

Relative movement of the flat surface 112 and the lens 124 towards and away from one another will cause the beam 121, which is at an angle to the flat surface 112, to move (up and down in FIG. 8) with respect to the flat surface. This movement will cause movement (up and down in FIG. 8) of the beam 130 and this will be detected by movement of the beam 128 at the position sensitive detector 132.

It will be understood that the point Fl, intermediate scan line 122, surface 112 and surface of detector 132 are conjugate (in all planes). The reflective surface of the mirror drum scanner 117 is conjugate with respect to these other conjugate points in a horizontal plane only.

In order to scan over a complete surface, in addition to scanning horizontally as shown in FIG. 7, the apparatus and the surface 112 may be moved relative to one another in a vertical direction.

In the description of FIGS. 7 and 8 we have referred to "vertical" and "horizontal". These are nominal and are used for convenience only. Of course, the apparatus may be disposed in other orientations.

The invention is not restricted to the details of the foregoing examples.

I claim:

1. Apparatus for measuring the distance from the apparatus to a surface comprising;

optical means for passing a beam of radiation to the surface at an angle other than normal;

optical means positioned to receive said beam of radiation after it has been specularly reflected from the surface;

means for measuring a position of the specularly reflected beam with respect to the optical axis of the second mentioned optical means whereby to indicate the distance from the part of the surface struck by the beam to the apparatus;

and means for scanning said beam across the surface.

2. Apparatus as claimed in claim 1 in which the across sectional size of the beam at the surface is substantially 5 micron.

3. Apparatus as claimed in claim 1 in which the optical axis of the second mentioned optical means is at right angles to the optical axis of the first mentioned optical means whereby, if the surface is at the focus of the second mentioned optical means, movement of the beam due to change of distance between the apparatus and the surface will be in the focal plane of the second mentioned optical means.

4. Apparatus as claimed in claim 1 in which automatic focusing means is provided so that the beam is focused on the surface at all times.

5. Apparatus as claimed in claim 1 in which the means for scanning the beam across the surface includes a rotatable mirror.

6. Apparatus as claimed in claim 1 in which the beam of radiation passing to the surface is initially focused at an intermediate scan line, the intermediate scan line and the surface being conjugate with respect to optical components between the intermediate scan line and the surface.

7. Apparatus as claimed in claim 1, in which the first and second mentioned optical menas are the same optical means.

8. Apparatus as claimed in claim 7, in which the beam of radiation passed to the surface by the optical means passes to the surface from one side of the optical axis of the optical means, and the beam of radiation received by the optical means from the surface after it has been specularly reflected passes to the optical means on the opposite side of the optical axis from the incident beam.

* * * * *